United States Patent [19]
Wingen et al.

[11] Patent Number: 5,648,021
[45] Date of Patent: Jul. 15, 1997

[54] PHENANTHRENE DERIVATIVES AND THEIR USE IN LIQUID-CRYSTALLINE MIXTURES

[75] Inventors: Rainer Wingen, Hattersheim; Barbara Hornung, Hasselroth, both of Germany

[73] Assignee: Hoechst Aktiengesellschaft, Frankfurt, Germany

[21] Appl. No.: 372,568

[22] Filed: Jan. 13, 1995

[30] Foreign Application Priority Data

Jan. 17, 1994 [DE] Germany ............... 44 01 004.4

[51] Int. Cl.$^6$ ............... C09K 19/32; C09K 19/34; C07D 239/02; C07D 211/70
[52] U.S. Cl. ............... 252/299.62; 252/299.61; 252/299.63; 544/298; 544/224; 546/339; 546/195; 568/647; 560/65
[58] Field of Search ............... 252/299.62, 299.61, 252/299.63; 560/65; 544/298, 224; 546/339, 195; 568/647

[56] References Cited

FOREIGN PATENT DOCUMENTS

| | | |
|---|---|---|
| 0455219 | 11/1991 | European Pat. Off. . |
| 015382 | 2/1982 | Germany . |
| 655323 | 4/1979 | U.S.S.R. . |
| 906387 | 2/1982 | U.S.S.R. . |
| 920062 | 4/1982 | U.S.S.R. . |
| 738516 | 6/1990 | U.S.S.R. . |

OTHER PUBLICATIONS

English Abstract of DE 4300435 published Jan. 17, 1992.
English Abstract of DE 3827046 published Aug. 10, 1988.
Chemical Abstract, vol. 82, 1975, Ref: 67566a.
Datenbank STN–CA, 1–50u. 1–91, On–Line–Ausdruck.
Chemistry and Industry, Aug. 3, 1974, pp. 615–616.
Tetrahedron, vol. 37, No. 16, 1981, pp. 2815–2821. This foreign language references contains an English language abstract on p. 2815.
English language abstract of Nippon Kagaku Kaishi, 1980, pp. 250–253.
J. Chemical Soc., Perkin 11, 1982, pp. 465–472.
J. Chemical Soc., 1958, pp. 552–555.
Pramana, Suppl. No. 1, 1975, pp. 397–414.

*Primary Examiner*—Cynthia Harris Kelly
*Attorney, Agent, or Firm*—Curtis Morris & Safford P.C.

[57] ABSTRACT

This invention relates to novel phenanthrene derivatives of the formula (I) which are particularly suitable for use in liquid-crystal mixtures. The compounds of formula (I) have a broad range of applications. Depending on the choice of substituents, they can be used as base materials from which liquid-crystalline phases are predominantly composed. They can also be added to liquid-crystalline base materials to modify the dielectric and/or optical anisotropy of a dielectric and to optimize its threshold voltage or viscosity. Liquid-crystalline mixtures containing compounds of formula (I) are particularly suitable for use in electrooptical switching and display devices.

7 Claims, No Drawings

PHENANTHRENE DERIVATIVES AND THEIR USE IN LIQUID-CRYSTALLINE MIXTURES

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in optoelectrical switching or display elements which have response times faster by a factor of up to 1000 compared with conventional TN ("twisted nematic") cells (cf., for example, EP-A 0 032 362). On the basis of this and other favorable properties, for example the possibility of bistable switching and the virtually viewing angle-independent contrast, FLCs are fundamentally highly suitable for areas of application such as computer displays.

For the use of FLCs in electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 μm) or even better is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved, for example, by adding one or more optically active dopes which induce a right-hand helix to the chiral liquid-crystal mixture which has, for example, a left-hand helix in the N* phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–134 and 114 (1984), 151–187). As in the case of the cholesteric pitch, this is achieved by using dopes having the opposite rotation of the helix.

The optical response time τ [μs] of ferroelectric liquid-crystal systems, which should be as short as possible, depends on the rotational viscosity of the system γ[mPas], the spontaneous polarization $P_s$[nC/cm²] and the electric field strength E[V/m], in accordance with the equation $$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ≈0.13, and a low positive or preferably negative dielectric anisotropy Δε are required (see, for example, S. T. Lagerwall et al., "Ferroelectric Liquid Crystals for Displays", SID Symposium, October Meeting 1985, San Diego, Calif., U.S.A.).

The totality of these requirements can only be achieved by means of mixtures comprising a plurality of components. The base (or matrix) used preferably comprises compounds which if possible themselves already have the desired phase sequence I→N→$S_A$→$S_C$. Further components of the mixture are frequently added in order to reduce the melting point and to broaden the $S_C$ and usually also the N phase, to induce optical activity, for pitch compensation and to match the optical and dielectric anisotropy; however, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

Derivatives of phenanthrene (which also include 9,10-dihydrophenanthrenes here) have already been described as liquid crystals or as components of liquid-crystalline mixtures:

azomethines containing a phenanthrene or 9,10-dihydrophenanthrene unit (J. Chem. Soc. [London] (1958) 552; J. chem. Soc., Perkin II (1982) 465); keto derivatives of 9,10-dihydrophenanthrene or of phenanthrene (Chem. Ind. [London] (1974) 615; Prod. Int. Liq. Cryst. Conf. (1973) 397; Tetrahedron 37, 2815 (1981)); carboxyl derivatives of 9,10-dihydrophenanthrene (DD-WP 153 826); 2,7-bis(alkoxy)phenanthrenes (Nippon Kagaku Kaishi (1980) 250) and 9,10-dihydrophenanthrenes containing mesogenic radicals in the 2,7-position (JP 05,262,744).

Since the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide novel compounds which are suitable in liquid-crystalline mixtures for improving the property profile of these mixtures.

It has been found that 2,7-disubstituted phenanthrene derivatives of the formula (I) are particularly suitable for use in liquid-crystal mixtures.

The invention therefore relates to compounds of the formula I

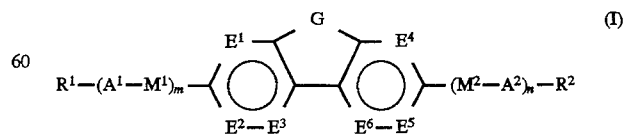

in which the symbols and indices have the following meanings:

$E^1$, $E^2$, $E^3$, $E^4$, $E^5$ and $E^6$ are —N—, —CF— or —CH—, with the following provisos:

if $E^1(E^4)$ is —N— or —CF—, $E^2$ and $E^3$ ($E^5$ and $E^6$) must be —CH—;

if $E^2$ and/or $E^3$ ($E^5$ and/or $E^6$) are —CF—, $E^1$ ($E^4$) must be —CH—;

if $E^2$ ($E^5$) is —N—, $E^1$ ($E^4$) must be —CH—, while $E^3$ ($E^6$) can be —CH— or —CF—;

and the proviso that at least one of $E^1$ to $E^6$ must be —N— or —CF—;

G is the —$CH_2CH_2$— or —CH=CH— group;

$R^1$ and $R^2$, independently of one another, are hydrogen, —CN, —F, —Cl, $CF_3$ or a straight-chain or branched alkyl radical having 1 to 20 carbon atoms (with or without asymmetrical carbon atoms), where one or more —$CH_2$— groups may also be replaced by —O—, —S—, —CO—, —CH=CH—, —C≡C—,

—$Si(CH_3)_2$—, 1,4-phenylene, trans-1,4-cyclohexylene or trans-1,3-cyclopentylene, with the proviso that oxygen atoms and sulfur atoms (referred to as chalcogens below) must not be bonded directly to one another, and/or one or more H atoms of the alkyl radical may be substituted by —F, —Cl, —Br or —$OR^3$, or are alternatively one of the following chiral groups:

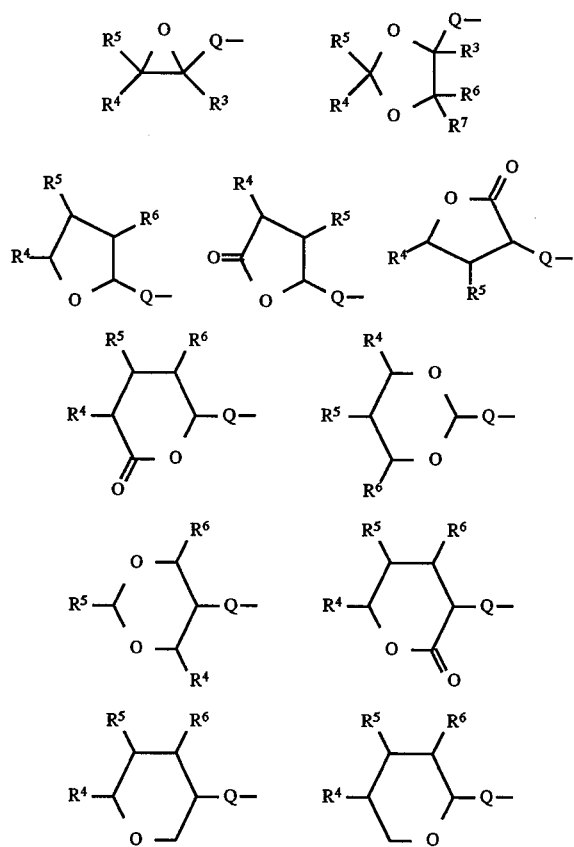

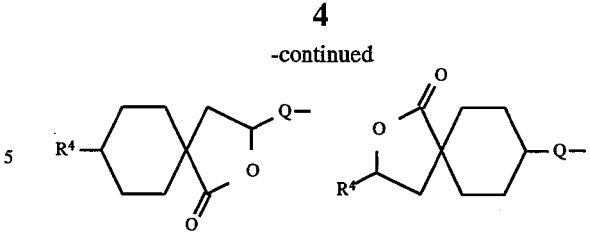

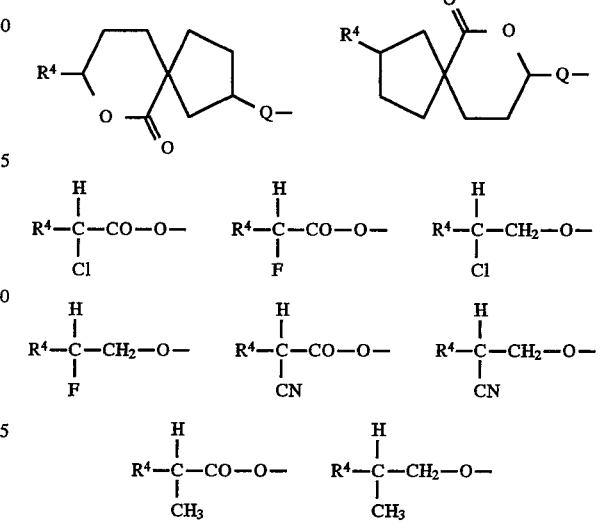

Preference is given to compounds of the formula (I) in which $R^1$ and $R^2$ are a straight-chain or branched alkyl radical (with or without an asymmetrical carbon atom) having 1 to 16 carbon atoms, where one or more —$CH_2$— groups may also be replaced by —O—,

or —$Si(CH_3)_2$—, with the proviso that chalcogens must not be bonded directly to one another, and/or one or more H atoms of the alkyl radical may be substituted by F; $R^1$ or $R^2$ can also be H, but not both simultaneously.

Particular preference is given to compounds of the formula (I) in which $R^1$ and $R^2$ are a straight-chain or branched alkoxy radical having 1 to 10 carbon atoms, where a —$CH_2$— group separated from the ring by at least two further —$CH_2$— groups can also be replaced by —$Si(CH_3)_2$—.

$R^3$, $R^4$, $R^5$, $R^6$ and $R^7$, independently of one another, are a straight-chain or branched alkyl radical having 1 to 16 carbon atoms (with or without asymmetrical carbon atoms), where one or more —$CH_2$— groups may also be replaced by —O— or —CH=CH—, with the proviso that oxygen atoms must not be bonded directly to one another, and/or one or more H atoms of the alkyl radical may be substituted by —F or —Cl; $R^4$ and $R^5$ may also together be —$(CH_2)_4$— or —$(CH_2)_5$— if they are bonded to an oxirane, dioxolane, tetrahydrofuran, tetrahydropyran, butyrolactone or valerolactone system;

Q is —$CH_2$—O—, —CO—O— or a single bond;

$M^1$ and $M^2$ are identical or different and are —CO—O—, —O—CO—, —$CH_2$—O—, —O—$CH_2$—, —$CH_2CH_2$—, —C≡C— or a single bond;

$A^1$ and $A^2$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, or 1,3-dioxaborinane-2,5-diyl;

n and m are zero or one, but add up to 1 at most.

If $R^1$ and/or $R^2$ are one of the optically active groups mentioned, m and n are preferably zero.

Preference is given to compounds of the formula (Ia) in which $E^1$ and/or $E^4$ is —N—,

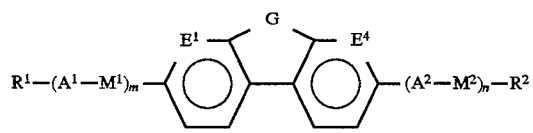 (Ia)

and of these, very particular preference is given to the compounds

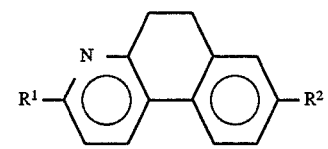 (Ia1)

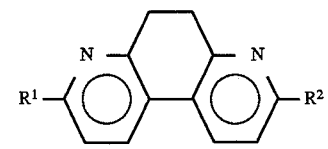 (Ia2)

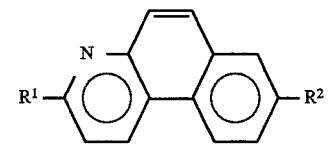 (Ia3)

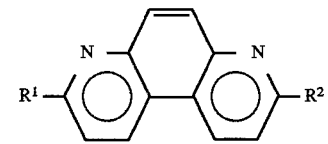 (Ia4)

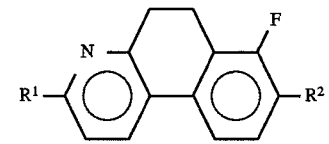 (Ia5)

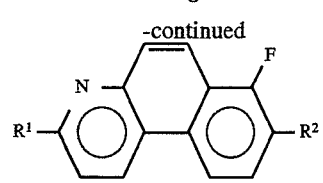 (Ia6)

Preference is furthermore given to the compounds of the formula (Ib) in which $E^2$ and/or $E^5$ are —N

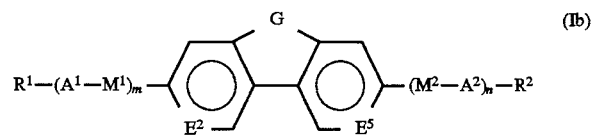 (Ib)

and of these, very particular preference is given to the compounds

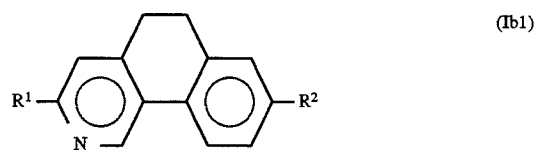 (Ib1)

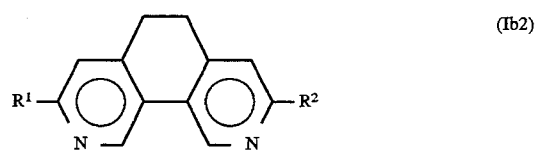 (Ib2)

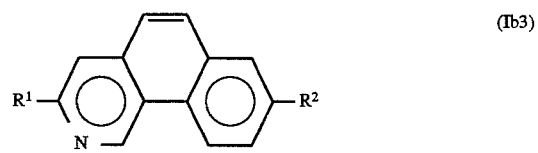 (Ib3)

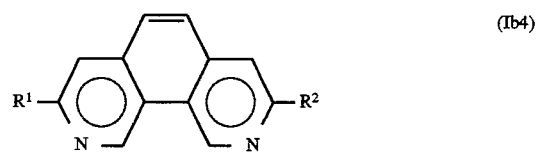 (Ib4)

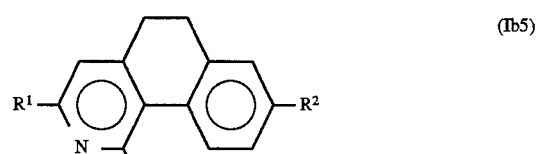 (Ib5)

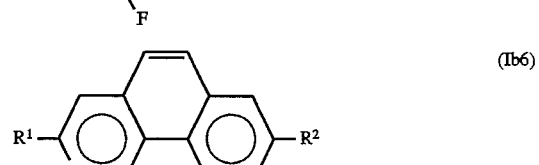 (Ib6)

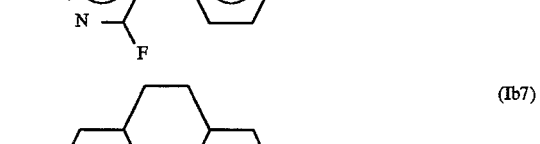 (Ib7)

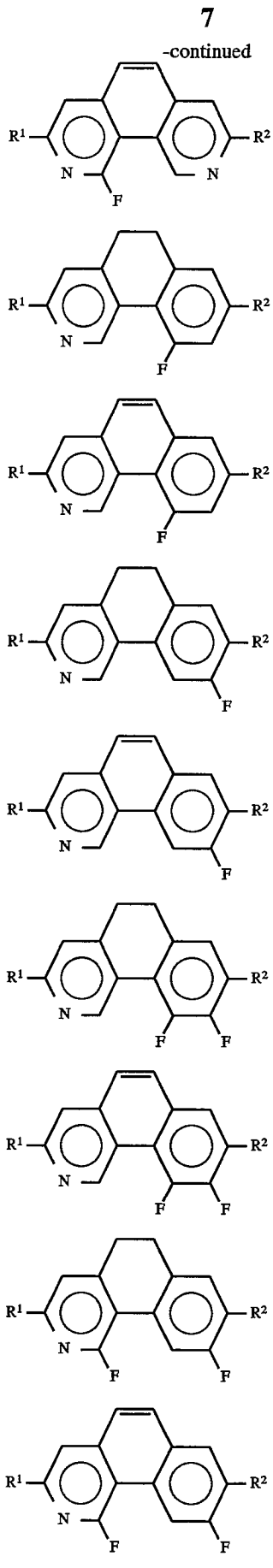

Preference is furthermore given to the compounds of the formula (Ic) in which $E^1$ and/or $E^4$ are —CF—

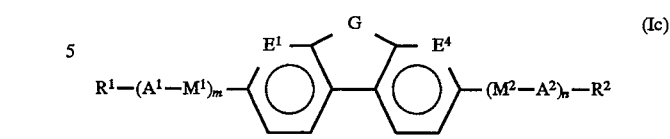

and of these, very particular preference is given to the compounds

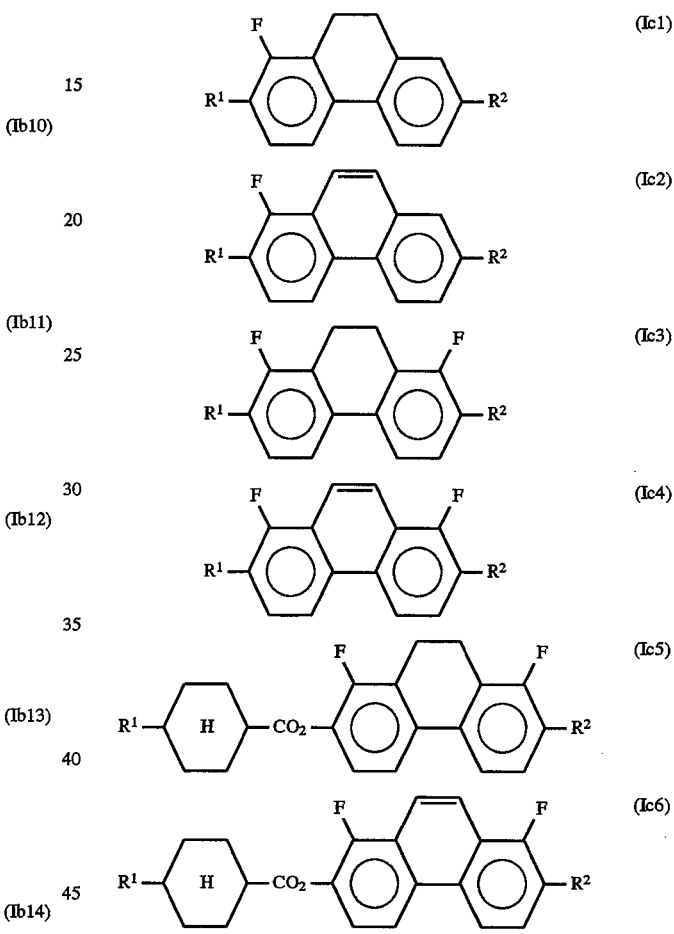

Preference is furthermore given to the compounds of the formula (Id) in which $E^1$ and $E^4$ are —CH— and $E^2$, $E^3$, $E^5$ and $E^6$ are —CH— or —CF—, but at least one is —CF—,

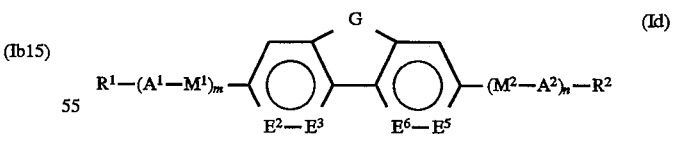

and of these, particular preference is given to the compounds

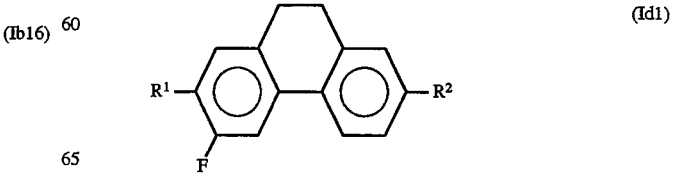

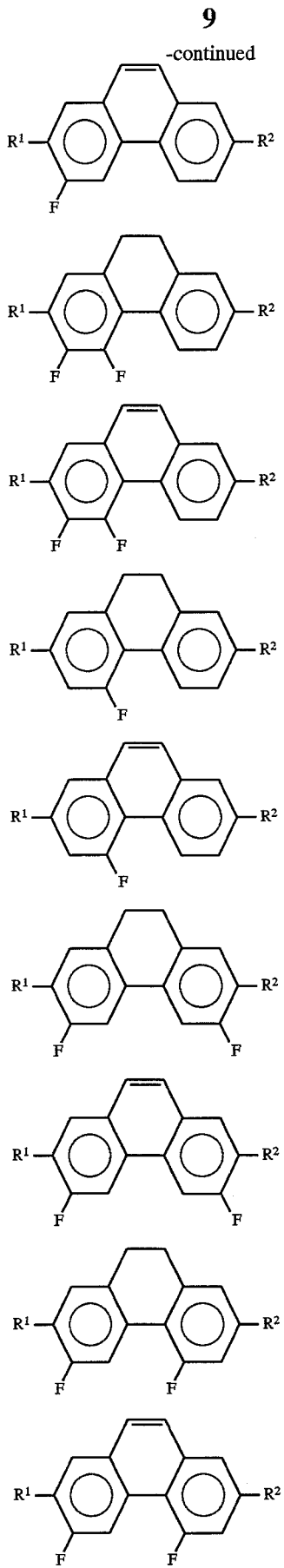
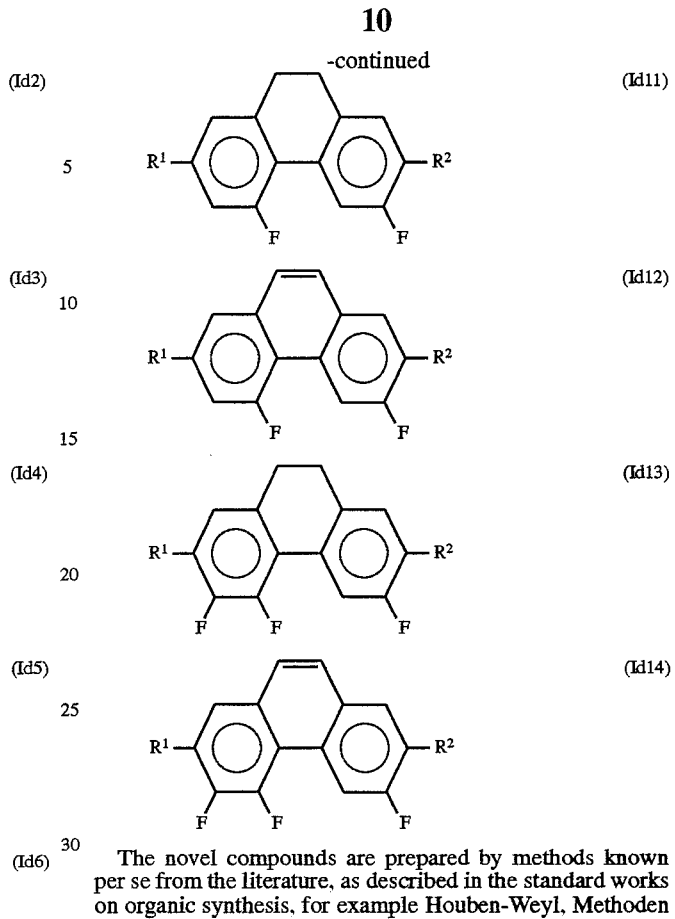

The novel compounds are prepared by methods known per se from the literature, as described in the standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use may also be made here of variants which are known per se, but are not mentioned here in greater detail.

For example, reference may be made to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981), pp. 513–519, DE-C-3 930 663, M. J. Sharp, W. Cheng and V. Snieckus in Tetrahedron Letters 28 (1987), pp. 5093 ff.; G. W. Gray in J. Chem. Soc. Perkin Trans. II, 1989, pp. 2041 ff. and Mol Cryst. Liq. Cryst. 172 (1989), pp. 165 ff., 204 (1991), pp. 43 ff. and pp. 91 ff.; EP-A 0 449 015; WO 89/12039; WO 89/03821; EP-A 0 354 434 for the direct linking of aromatic and heteroaromatic rings; DE-A 32 01 721 for compounds containing —CH$_2$CH$_2$— bridges, and Koji Seto et al. in Liquid Crystals 8 (1990), pp. 861–870 for compounds containing —C≡C— bridges.

The preparation of disubstituted pyridines, disubstituted pyrazines, disubstituted pyrimidines and disubstituted pyridazines is given, for example, in the appropriate volumes of the series "The Chemistry of Heterocyclic Compounds" by A. Weissberger and E. C. Taylor (Editors).

If desired, the starting materials can also be formed in situ by not isolating them from the reaction mixture, but instead immediately converting them further into the compounds of the formula (I).

Schemes 1 and 2 show by way of example synthetic routes to compounds of types (Ia2) and (Ia4); an analogous procedure is also possible for the other compounds of type (Ia).

Type (Ic) is in principle accessible as shown in scheme 3. By using appropriate units, either at the aldehyde or the triphenylphosphonium salt stage, the asymmetrical structures (Ic1) and (Ic2) are also obtainable. It is furthermore possible to provide one of the substituents R with protecting group or position-holding characteristics (for example as benzoxy), so that this group can be removed at a suitable point in the synthesis (for example after step "i"), with the aim, for example, of obtaining compounds of type (Ic5) or (Ic6) by esterification by means of an $R^1$-substituted cyclohexanecarboxylic acid. Symmetrical (for example Ib4) and asymmetrical (for example Ib1) compounds of type (Ib) are obtainable, for example, as shown in scheme 4; at the 1,2-substituted ether stage, the E/Z-mixture obtained from step "f" can also be employed both for the photochemical cyclization (step "g") and also advantageously for step "h".

Scheme 5 describes another route to compounds of type (Ia), which is outlined here for symmetrical structures, but is particularly advantageous for asymmetrical compounds.

Scheme 1

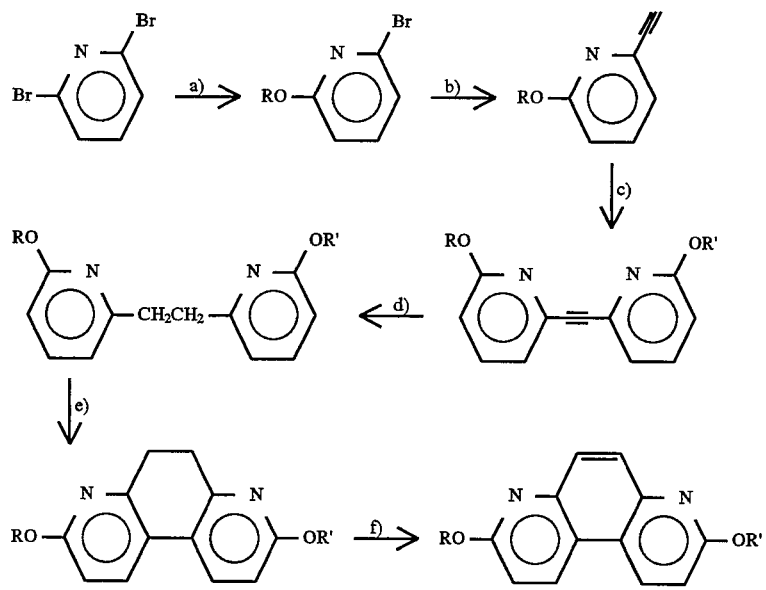

a) NaOR in ROH
b) H —C ≡ C-Tms, HN(iPr)$_2$, Pd(II)/Cu(I) catalyst, analogously to J. Organomet, Chem. 453 (1993) 2, C 19
c) HN(Pr)$_2$, Pd(O) catalyst, analogously to J. Organomet. Chem. 453 (1993) 2, C 19
d) H$_2$/catalyst (cf. P.N. Rylander, Hydrogenation Methods, Academic Press, London, 1985, p. 53)
e) Pt/C; for example analogously to Zelensky, Tietz, Berichte 62, 2869 (1929)
f) for example using 2,3-dichloro-5,6-dicyanobenzoquinone, analogously to J. Chem, Soc. 1954, 3569

Scheme 2

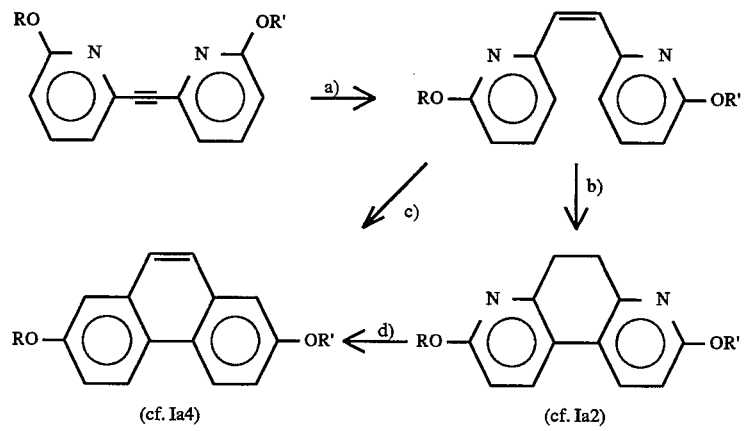

Scheme 3

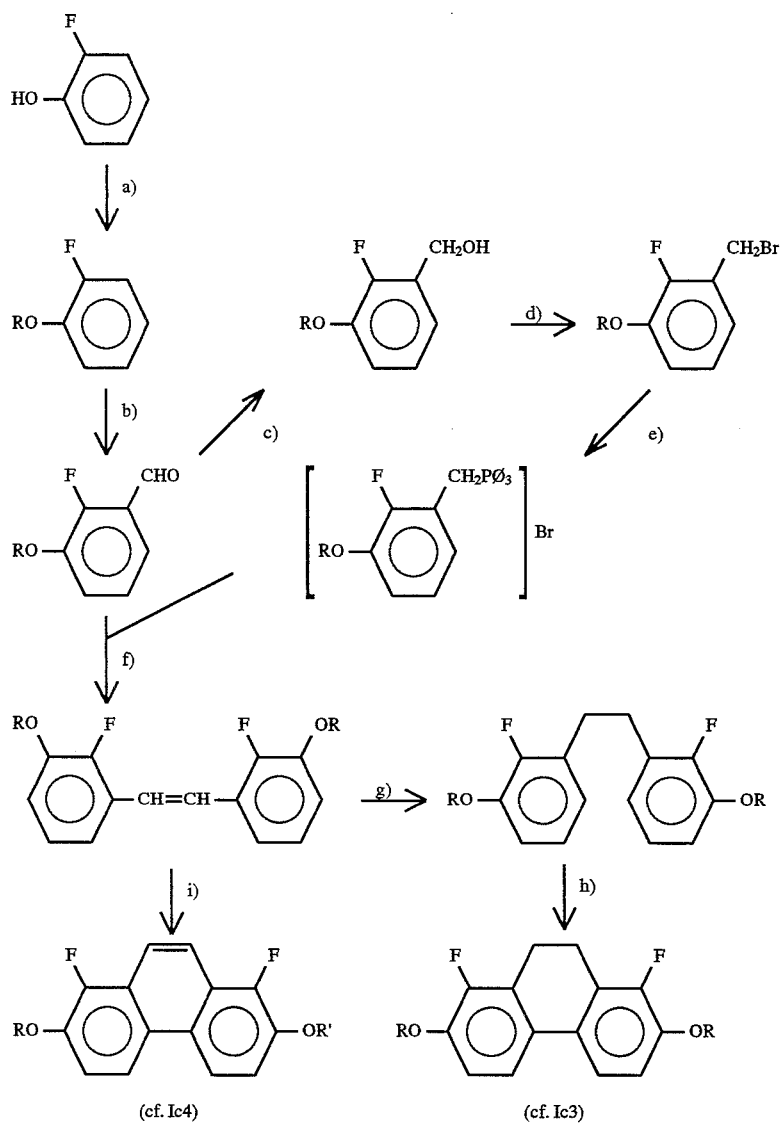

a) Base/RX
b) 1. LDA 2. DMF 3. H⁺; analogously to J. Org. Chem. 51, 3762 (1986)
c) LiAlH₄ (cf. Angew. Chem. 68, 601 (1956))
d) cf. R.C. Larock, Comprehensive Organic Transformations, VCH Publishers, New York, 1989, pp. 353
e) Ø₃P, for example analogously to Org. Reactions 14, 388 (1965)
f) cf. Org. Reactions 14, 270 (1965)
g) H₂/catalyst (cf. P.N. Rylander, Hydrogenation Methods, Academic Press, London, 1985, p. 23)
h) Pt/catalyst; for example analogously to Zelinsky, Tietz, Ber. 62, 2869 (1929)
i) hγ/I₂; for example analogously to J. Am. Chem. Soc. 84, 4361 (1962)

Scheme 4

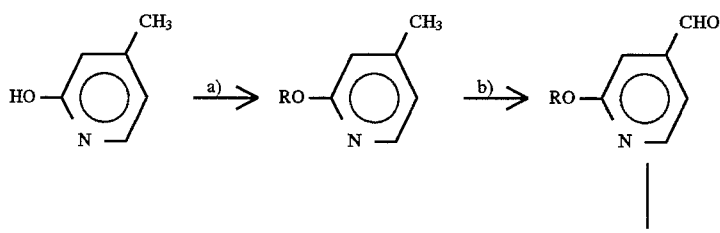

-continued
Scheme 4
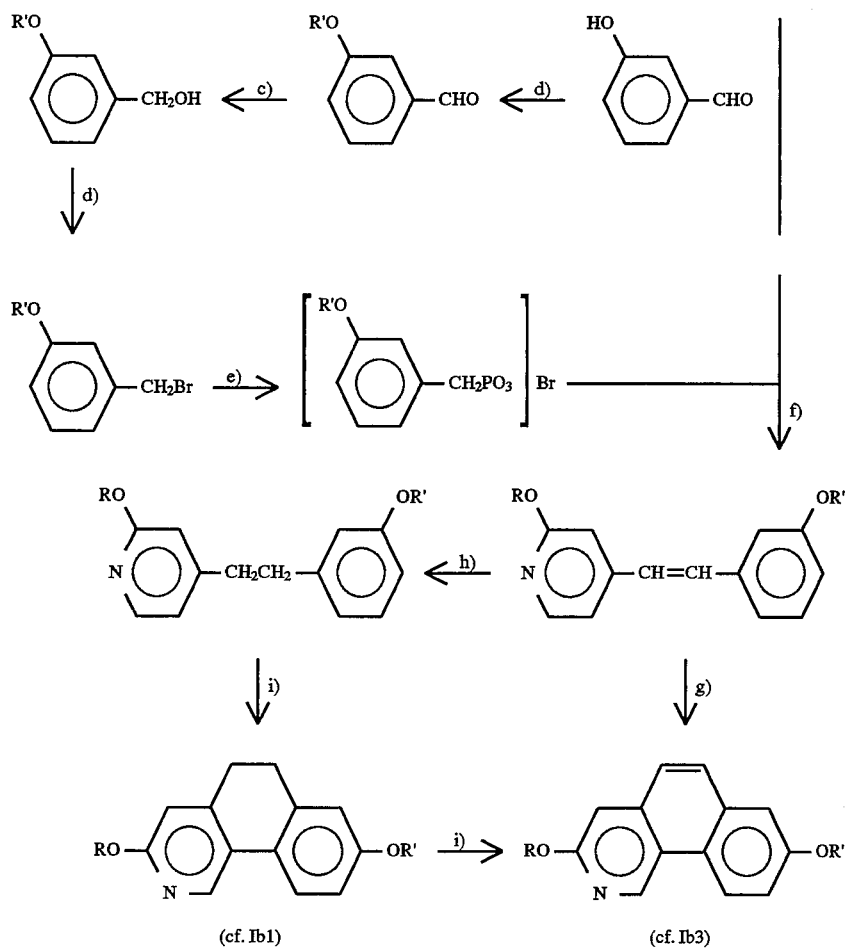
Scheme 5
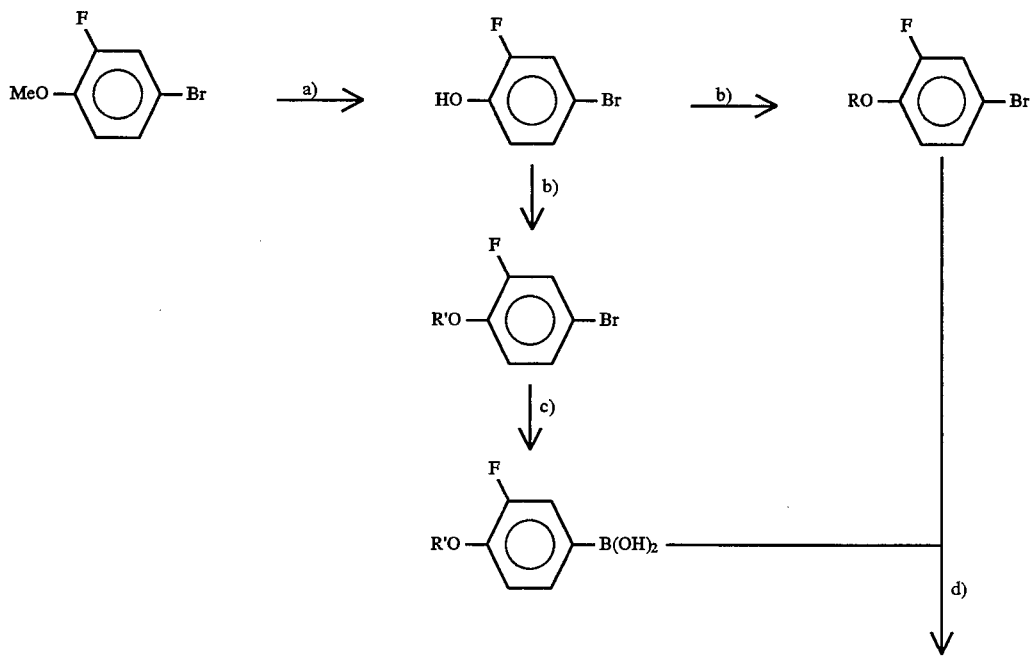

-continued
Scheme 5

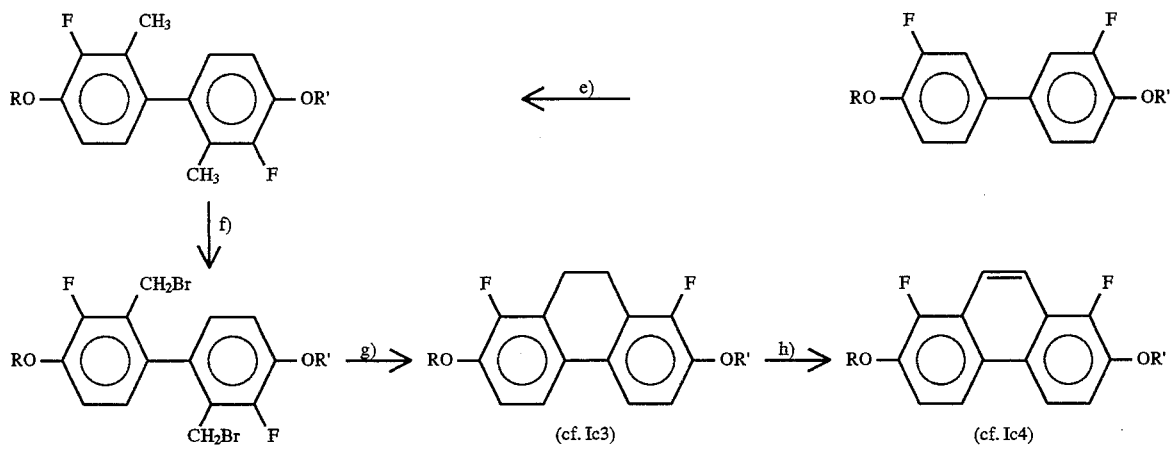

The synthesis of the $R^1$—$(A^1$—$M^1)_m$ and $(M^2$—$A^2)_n$—$R^2$ radicals or suitable reactive derivatives thereof or other suitable precursors of this group is carried out by methods known to the person skilled in the art.

The preparation is carried out under reaction conditions which are known and suitable for said reactions. Use may also be made of variants which are known per se, but are not described here in greater detail.

For example, reference may be made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; EP-A 309 514 for compounds containing 1,3,4-thiadiazole-2,5-diyl groups; WO-A 92/16500 for naphthalene-2,6-diyl groups; DE-A 37 10 890 for bicyclo[2.2.2]octane-1,4-diyl groups; K. Seto et al., Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann.

As far as the linking of ring systems to one another is concerned, reference may be made, for example, to: N. Miyaura, T. Yanagai and A. Suzuki in Synthetic Communications 11 (1981), 513–519 DE-C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —$CH_2CH_2$— bridges, and Koji Seto et el. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCCI method (DCCI= dicyclohexylcarbodiimide).

The corresponding carboxylic acids and alcohols or phenols are known and can be prepared analogously to known processes.

Particularly suitable reactive derivatives of the said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the corresponding alkyl halide, sulfonate or dialkyl sulfate, expediently in an inert solvent, such as acetone, 1,2-dimethoxyethane, DMF or dimethyl sulfoxide, or alternatively with an excess of aqueous or aqueous/alcoholic NaOH or KOH at temperatures between about 20° and 100° C.

Regarding the synthesis of specific radicals $R^1$, reference may additionally be made, for example, to EP-A 0 355 008 for compounds containing silicon-containing side chains and to EP-A 0 292 954 and EP-A 0 398 155 for compounds containing cyclopropyl groups in the side chain.

The provision of compounds of the formula (I) very generally considerably broadens the range of liquid-crystalline substances which are suitable, from various application points of view, for the preparation of liquid-crystalline mixtures.

In this connection, the compounds of the formula (I) have a broad range of applications. Depending on the choice of substituents, they can be used as base materials from which liquid-crystalline phases are predominantly composed; however, compounds of the formula (I) can also be added to liquid-crystalline base materials from other classes of compound, in order, for example, to modify the dielectric and/or optical anisotropy of a dielectric of this type and/or to optimize its threshold voltage and/or its viscosity. The compounds of the formula (I) are particularly suitable for modifying the dielectric anisotropy, $\Delta\epsilon$, towards higher negative values even when added in small amounts.

The invention also relates to the use of compounds of the formula (I) in liquid-crystal mixtures, preferably in ferroelectric, antiferroelectric and nematic mixtures, in particular in ferroelectric and antiferroelectric mixtures.

The invention furthermore relates to liquid-crystal mixtures, preferably ferroelectric, antiferroelectric and nematic mixtures, in particular ferroelectric and antiferroelectric mixtures, containing one or more compounds of the formula (I), preferably of the formula (Ia).

The liquid-crystal mixtures according to the invention generally contain from 2 to 35, preferably from 2 to 25, particularly preferably from 2 to 20 components.

They generally contain from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures containing compounds of the formula (I) according to the invention are preferably selected from known compounds having smectic and/or nematic and/or cholesteric and/or antiferroelectric phases. These include, for example:

- derivatives of phenylpyrimidine, as described, for example, in WO 86/06401 and U.S. Pat. No. 4,874,542,
- meta-substituted aromatic compounds having a six-membered ring, as described, for example, EP-A 0 578 054,
- silicon compounds, as described, for example, in EP-A 0 355 008,
- mesogenic compounds containing only one side chain as described in EP-A 0 541 081,
- hydroquinone derivatives, as described, for example, in EP-A 0 603 788,
- pyridylpyrimidines, as described, for example, in WO 92/12974,
- phenylbenzoates, as described, for example, in P. Keller, Ferroelectrics, 1984. 58, 3, and J. W. Goodby et al., Liquid Crystals and Ordered Fluids, Vol. 4, New York, 1984, and
- thiadiazoles as described, for example, in EP-B 309 514.

Examples of suitable chiral, non-racemic dopes are:

- optically active phenylbenzoates, as described, for example, in P. Keller, Ferroelectrics 58 (1984), 3, and J. W. Goodby et al., Liquid Crystals and Ordered Fluids, Vol. 4, New York, 1984,
- optically active oxirane ethers, as described, for example, in EP-A 0 263 437 and WO-A 93/13093,
- optically active oxirane esters, as described, for example, in EP-A 0 292 954,
- optically active dioxolane ethers, as described, for example, in EP-A 0 351 746,
- optically active dioxolane esters, as described, for example, in EP-A 0 361 272, and
- optically active tetrahydrofuran-2-carboxylic esters, as described, for example, in EP-A 0 355 561.

The mixtures can in turn be used in electro-optical or fully optical elements, for example display elements, switching elements, light modulators, elements for image processing and/or signal processing or generally in the area of nonlinear optics.

Liquid-crystalline mixtures containing compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

The present invention is described in greater detail with reference to the examples below:

EXAMPLE 1

1,8-Difluoro-2,7-dioctyloxyphenanthrene

A solution of 2.5 g of 2-fluoro-3-octyloxybenzaldehyde (prepared by reacting 2-octyloxyfluorobenzene with lithium diisopropylamide followed by reaction with N,N-dimethylformamide) in 50 ml of THF is added dropwise at 20° C. to a fully reacted mixture of 5.6 g of 2-fluoro-3-octyloxybenzyltriphenylphosphoniumbromide (prepared by the reaction sequence: reaction of 2-fluoro-3-octyloxybenzaldehyde with $LiAlH_4$ in THF to give fluoro-3-octyloxybenzyl alcohol, reaction of the latter with triphenylphosphine/$Br_2$ to give 2-fluoro-3-octyloxybenzyl bromide and reaction of the latter with triphenylphosphine in toluene) and 1.2 g of potassium tert-butoxide in 100 ml of THF. When the reaction is complete, the mixture is adjusted to pH 5 using HCl, 500 ml of $H_2O$ are added, and the mixture is extracted three times with 100 ml of diethyl ether in each case. Chromatography on silica gel using dichloromethane/heptane 1:1 gives 1,2-bis(2-fluoro-3-octyloxyphenyl)ethene as an E/Z-mixture. The latter is dissolved in cyclohexane, 4 mol % of iodine are added, and the mixture is exposed to UV light for 8 hours at 25° C. in a quartz apparatus. Chromatography on $SiO_2$ using dichloromethane and recrystallization from acetonitrile give 1.2 g of 1,8-difluoro-2,7-dioctyloxyphenanthrene as colorless crystals.

The following are obtained analogously to Example 1:

EXAMPLE 2
1,8-difluoro-2,7-dibutoxyphenanthrene

EXAMPLE 3
1,8-difluoro-2,7-dipentoxyphenanthrene

EXAMPLE 4
1,8-difluoro-2,7-dihexyloxyphenanthrene; phase sequence X 74 $S_A$ 123 I

EXAMPLE 5
1,8-difluoro-2,7-diheptyloxyphenanthrene

EXAMPLE 6
1,8-difluoro-2,7-dinonyloxyphenanthrene

EXAMPLE 7
1,8-difluoro-2,7-didecyloxyphenanthrene

EXAMPLE 8
1,8-difluoro-2,7-diundecyloxyphenanthrene

EXAMPLE 9
1,8-difluoro-2,7-didodecyloxyphenanthrene

EXAMPLE 10
1,8-difluoro-2-butoxy-7-pentoxyphenanthrene

EXAMPLE 11
1,8-difluoro-2-butoxy-7-hexyloxyphenanthrene

EXAMPLE 12
1,8-difluoro-2-butoxy-7-heptoxyphenanthrene

EXAMPLE 13
1,8-difluoro-2-butoxy-7-octyloxyphenanthrene

EXAMPLE 14
1,8-difluoro-2-butoxy-7-nonyloxyphenanthrene

EXAMPLE 15
1,8-difluoro-2-pentoxy-7-propoxyphenanthrene

EXAMPLE 16
1,8-difluoro-2-pentoxy-7-hexyloxyphenanthrene

EXAMPLE 17
1,8-difluoro-2-pentoxy-7-heptyloxyphenanthrene

EXAMPLE 18
1,8-difluoro-2-pentoxy-7-octyloxyphenanthrene

EXAMPLE 19
1,8-difluoro-2-pentoxy-7-nonyloxyphenanthrene

EXAMPLE 20
1,8-difluoro-2-hexyloxy-7-propoxyphenanthrene

EXAMPLE 21
1,8-difluoro-2-hexyloxy-7-heptyloxyphenanthrene

EXAMPLE 22
1,8-difluoro-2-hexyloxy-7-octyloxyphenanthrene

EXAMPLE 23
1,8-difluoro-2-hexyloxy-7-nonyloxyphenanthrene

EXAMPLE 24
1,8-difluoro-2-hexyloxy-7-decyloxyphenanthrene

EXAMPLE 25
1,8-difluoro-2-hexyloxy-7-dodecyloxyphenanthrene

EXAMPLE 26
1,8-difluoro-2-heptyloxy-7-propoxyphenanthrene

EXAMPLE 27
1,8-difluoro-2-heptyloxy-7-octyloxyphenanthrene

EXAMPLE 28
1,8-difluoro-2-heptyloxy-7-nonyloxyphenanthrene

EXAMPLE 29
1,8-difluoro-2-octyloxy-7-ethoxyphenanthrene

EXAMPLE 30
1,8-difluoro-2-octyloxy-7-propoxyphenanthrene

EXAMPLE 31
1,8-difluoro-2-octyloxy-7-nonyloxyphenanthrene

EXAMPLE 32
1,8-difluoro-2-octyloxy-7-decyloxyphenanthrene

EXAMPLE 33
1,8-difluoro-2-nonyloxy-7-ethoxyphenanthrene

EXAMPLE 34
1,8-difluoro-2-nonyloxy-7-propoxyphenanthrene

EXAMPLE 35
1,8-difluoro-2-nonyloxy-7-decyloxyphenanthrene

EXAMPLE 36
1,8-difluoro-2-decyloxy-7-methoxyphenanthrene

EXAMPLE 37
1,8-difluoro-2-decyloxy-7-ethoxyphenanthrene

EXAMPLE 38
1,8-difluoro-2-decyloxy-7-propoxyphenanthrene

EXAMPLE 39
1,8-difluoro-2-decyloxy-7-butoxyphenanthrene

EXAMPLE 40
1,8-difluoro-2-decyloxy-7-pentoxyphenanthrene

EXAMPLE 41
1,8-difluoro-2-decyloxy-7-heptyloxyphenanthrene

EXAMPLE 42
1-fluoro-2,7-dibutoxyphenanthrene

EXAMPLE 43
1-fluoro-2,7-dipentoxyphenanthrene

EXAMPLE 44
1-fluoro-2,7-dihexyloxyphenanthrene

EXAMPLE 45
1-fluoro-2,7-diheptyloxyphenanthrene

EXAMPLE 46
1-fluoro-2,7-dioctyloxyphenanthrene

EXAMPLE 47
1-fluoro-2,7-dinonyloxyphenanthrene

EXAMPLE 48
1-fluoro-2,7-didecyloxyphenanthrene

EXAMPLE 49
1-fluoro-2,7-diundecyloxyphenanthrene

EXAMPLE 50
1-fluoro-2,7-didodecyloxyphenanthrene

EXAMPLE 51
1-fluoro-2-butoxy-7-pentoxyphenanthrene

EXAMPLE 52
1-fluoro-2-butoxy-7-hexyloxyphenanthrene

EXAMPLE 53
1-fluoro-2-butoxy-7-heptyloxyphenanthrene

EXAMPLE 54
1-fluoro-2-butoxy-7-octyloxyphenanthrene

EXAMPLE 55
1-fluoro-2-butoxy-7-nonyloxyphenanthrene

EXAMPLE 56
1-fluoro-2-butoxy-7-decyloxyphenanthrene

EXAMPLE 57
1-fluoro-2-pentoxy-7-hexyloxyphenanthrene

EXAMPLE 58
1-fluoro-2-pentoxy-7-heptyloxyphenanthrene

EXAMPLE 59
1-fluoro-2-pentoxy-7-octyloxyphenanthrene

EXAMPLE 60
1-fluoro-2-pentoxy-7-nonyloxyphenanthrene

EXAMPLE 61
1-fluoro-2-hexyloxy-7-butoxyphenanthrene

EXAMPLE 62
1-fluoro-2-hexyloxy-7-pentoxyphenanthrene

EXAMPLE 63
1-fluoro-2-hexyloxy-7-heptyloxyphenanthrene

EXAMPLE 64
1-fluoro-2-hexyloxy-7-octyloxyphenanthrene

EXAMPLE 65
1-fluoro-2-hexyloxy-7-nonyloxyphenanthrene

EXAMPLE 66
1-fluoro-2-hexyloxy-7-decyloxyphenanthrene

EXAMPLE 67
1-fluoro-2-heptyloxy-7-propoxyphenanthrene

EXAMPLE 68
1-fluoro-2-heptyloxy-7-butoxyphenanthrene

EXAMPLE 69
1-fluoro-2-heptyloxy-7-pentoxyphenanthrene

EXAMPLE 70
1-fluoro-2-heptyloxy-7-octyloxyphenanthrene

EXAMPLE 71
1-fluoro-2-heptyloxy-7-nonyloxyphenanthrene

EXAMPLE 72
1-fluoro-2-heptyloxy-7-decyloxyphenanthrene

EXAMPLE 72A
1-fluoro-2-octyloxyphenanthrene; m.p. 91° C.

EXAMPLE 73
1-fluoro-2-octyloxy-7-propoxyphenanthrene

EXAMPLE 74
1-fluoro-2-octyloxy-7-butoxyphenanthrene

EXAMPLE 75
1-fluoro-2-octyloxy-7-pentoxyphenanthrene

EXAMPLE 76

1-fluoro-2-octyl-7-hexyloxyphenanthrene; phase sequence: X 95 $S_2$ 113 $S_A$ 127 I

EXAMPLE 77

1-fluoro-2-octyloxy-7-octyloxyphenanthrene

EXAMPLE 78

1-fluoro-2-octyloxy-7-nonyloxyphenanthrene

EXAMPLE 79

1-fluoro-2-octyloxy-7-decyloxyphenanthrene

EXAMPLE 80

1-fluoro-2-octyloxy-7-undecyloxyphenanthrene

EXAMPLE 81

1-fluoro-2-nonyloxy-7-propoxyphenanthrene

EXAMPLE 82

1-fluoro-2-nonyloxy-7-butoxyphenanthrene

EXAMPLE 83

1-fluoro-2-nonyloxy-7-pentoxyphenanthrene

EXAMPLE 84

1-fluoro-2-nonyloxy-7-hexyloxyphenanthrene

EXAMPLE 85

1-fluoro-2-nonyloxy-7-heptyloxyphenanthrene

EXAMPLE 86

1-fluoro-2-nonyloxy-7-octyloxyphenanthrene

EXAMPLE 87

1-fluoro-2-nonyloxy-7-decyloxyphenanthrene

EXAMPLE 88

2,7-bis(hexyloxy)-1,8-diazaphenanthrene

A mixture of 7.7 g of 2-bromo-6-hexyloxypyridine (prepared by reacting 2,6-dibromopyridine with sodium hexoxide in DMF), 3.9 g of trimethylsilylacetylene, 0.4 g of bis(triphenylphosphine)palladium(II) chloride and 0.05 g of copper (I) iodide in 100 ml of diethylamine is stirred at 20° C. for 12 hours. After the volatile constituents have been removed in a rotary evaporator, the mixture is filtered through $SiO_2$ using dichloromethane; the crude 1-(2-bromopyridin-6-yl)-2-trimethylsilylethtne (7.5 g of melting point 24° to 27° C.) obtained is stirred for 1 hour at 20° C. in 100 ml of methanol with 25 ml of 1N aqueous NaOH solution. The solvent is evaporated, and the residue is chromatographed over $SiO_2$ using dichloromethane/heptane 9:1, giving 4.3 g of 2-bromo-6-ethynylpyridine (brownish oil). A solution of 2 g of 2-bromo-6-ethynylpyridine in 50 ml of benzene to which 2.6 g of 2-bromo-6-hexyloxypyridine, 0.2 g of tetrakis(triphenylphisphine)palladium(0) and 30 ml of n-propylamine have been added is stirred at 20° C. for 10 hours. The volatile constituents are removed by distillation, and the residue is chromatographed over $SiO_2$ using dichloromethane, giving 1.9 g of 1,2-bis(2-hexyloxypyridin-6-yl)ethyne. The latter is hydrogenated quantitatively in 50 ml of THF using Lindlar catalyst [Org. Synth. 46, 89 (1966)] to 1,2-bis(2-hexyloxypyridin-6-yl)ethene. The latter is dissolved in 500 ml of cyclohexane, 4 mol % of iodine are added, and the mixture is exposed to UV light for 10 hours at 25° C. in a quartz apparatus. Chromatography on $SiO_2$ using dichloromethane and recrystallization from acetonitrile give 0.9 g of 2,7-bis(hexyloxy)-1,8-diazaphenanthrene as colorless crystals of melting point 91° C.

The following are obtained analogously to Example 88:

EXAMPLE 89

2,7-bis(pentoxy)-1,8-diazaphenanthrene

EXAMPLE 90

2,7-bis(heptyloxy)-1,8-diazaphenanthrene

EXAMPLE 91

2,7-bis(octyloxy)-1,8-diazaphenanthrene

EXAMPLE 92

2,7-bis(nonyloxy)-1,8-diazaphenanthrene

EXAMPLE 93

2,7-bis(decyloxy)-1,8-diazaphenanthrene

EXAMPLE 94

2,7-bis(undecyloxy)-1,8-diazaphenanthrene

EXAMPLE 95

2,7-bis(dodecyloxy)-1,8-diazaphenanthrene

EXAMPLE 96

2-butoxy-7-pentoxy-1,8-diazaphenanthrene

EXAMPLE 97

2-butoxy-7-hexyloxy-1,8-diazaphenanthrene

EXAMPLE 98

2-butoxy-7-heptyloxy-1,8-diazaphenanthrene

EXAMPLE 99

2-butoxy-7-octyloxy-1,8-diazaphenanthrene

EXAMPLE 100

2-butoxy-7-nonyloxy-1,8-diazaphenanthrene 5

EXAMPLE 101

2-butoxy-7-decyloxy-1,8-diazaphenanthrene

EXAMPLE 102

2-pentoxy-7-hexyloxy-1,8-diazaphenanthrene; m.p. 82° C.

EXAMPLE 103

2-pentoxy-7-heptyloxy-1,8-diazaphenanthrene

EXAMPLE 104

2-pentoxy-7-octyloxy-1,8-diazaphenanthrene

EXAMPLE 105
2-pentoxy-7-nonyloxy-1,8-diazaphenanthrene

EXAMPLE 106
2-pentoxy-7-decyloxy-1,8-diazaphenanthrene

EXAMPLE 107
2-hexyloxy-7-heptyloxy-1,8-diazaphenanthrene

EXAMPLE 108
2-hexyloxy-7-octyloxy-1,8-diazaphenanthrene; m.p. 72° C.

EXAMPLE 109
2-hexyloxy-7-nonyloxy-1,8-diazaphenanthrene

EXAMPLE 110
2-hexyloxy-7-decyloxy-1,8-diazaphenanthrene

EXAMPLE 111
2-hexyloxy-7-(4-butyldimethylsilyl)butoxy-1,8-diazaphenanthrene

EXAMPLE 111A
2-hexyloxy-1,8-diazaphenanthrene; m.p. 80° C.

EXAMPLE 111B
2-hexyloxy-7-methyl-1,8-diazaphenanthrene; m.p. 67° C.

EXAMPLE 112
2-heptyloxy-7-octyloxy-1,8-diazaphenanthrene

EXAMPLE 113
2-heptyloxy-7-nonyloxy-1,8-diazaphenanthrene

EXAMPLE 114
2-heptyloxy-7-decyloxy-1,8-diazaphenanthrene

EXAMPLE 115
2-heptyloxy-7-(6-methyl)octyloxy-1,8-diazaphenanthrene

EXAMPLE 116
2-octyloxy-7-nonyloxy-1,8-diazaphenanthrene

EXAMPLE 117
2-octyloxy-7-decyloxy-1,8-diazaphenanthrene

EXAMPLE 118
2-octyloxy-7-undecyloxy-1,8-diazaphenanthrene

EXAMPLE 119
2-octyloxy-7-dodecyloxy-1,8-diazaphenanthrene

EXAMPLE 120
2-octyloxy-7-(5-oxa)nonyloxy-1,8-diazaphenanthrene

EXAMPLE 121
2-nonyloxy-7-decyloxy-1,8-diazaphenanthrene

EXAMPLE 122
2-nonyloxy-7-undecyloxy-1,8-diazaphenanthrene

EXAMPLE 123
2-nonyloxy-7-dodecyloxy-1,8-diazaphenanthrene

EXAMPLE 124
2-decyloxy-7-undecyloxy-1,8-diazaphenanthrene

EXAMPLE 125
2-decyloxy-7-dodecyloxy-1,8-diazaphenanthrene

EXAMPLE 126
2-butoxy-7-pentoxy-1-azaphenanthrene

EXAMPLE 127
2-butoxy-7-hexyloxy-1-azaphenanthrene

EXAMPLE 128
2-butoxy-7-heptyloxy-1-azaphenanthrene

EXAMPLE 129
2-butoxy-7-octyloxy-1-azaphenanthrene

EXAMPLE 130
2-butoxy-7-nonyloxy-1-azaphenanthrene

EXAMPLE 131
2-butoxy-7-decyloxy-1-azaphenanthrene

EXAMPLE 132
2-pentoxy-7-hexyloxy-1-azaphenanthrene

EXAMPLE 133
2-pentoxy-7-heptyloxy-1-azaphenanthrene

EXAMPLE 134
2-pentoxy-7-octyloxy-1-azaphenanthrene

EXAMPLE 135
2-pentoxy-7-nonyloxy-1-azaphenanthrene

EXAMPLE 136
2-pentoxy-7-decyloxy-1-azaphenanthrene

EXAMPLE 137
2-hexyloxy-7-heptyloxy-1-azaphenanthrene

EXAMPLE 138
2-hexyloxy-7-octyloxy-1-azaphenanthrene

EXAMPLE 139
2-hexyloxy-7-nonyloxy-1-azaphenanthrene

EXAMPLE 140
2-hexyloxy-7-decyloxy-1-azaphenanthrene

EXAMPLE 141

2-hexyloxy-7-(4-butyldimethylsilyl)butoxy-1-azaphenanthrene

EXAMPLE 142

2-heptyloxy-7-octyloxy-1-azaphenanthrene

EXAMPLE 143

2-heptyloxy-7-nonyloxy-1-azaphenanthrene

EXAMPLE 144

2-heptyloxy-7-decyloxy-1-azaphenanthrene

EXAMPLE 145

2-heptyloxy-7-(6-methyl)octyloxy-1-azaphenanthrene

EXAMPLE 146

2-octyloxy-7-nonyloxy-1-azaphenanthrene

EXAMPLE 147

2-octyloxy-7-decyloxy-1-azaphenanthrene

EXAMPLE 148

2-octyloxy-7-undecyloxy-1-azaphenanthrene

EXAMPLE 149

2-octyloxy-7-dodecyloxy-1-azaphenanthrene

EXAMPLE 150

2-octyloxy-7-(5-oxa)nonyloxy-1-azaphenanthrene

EXAMPLE 151

2-nonyloxy-7-decyloxy-1-azaphenanthrene

EXAMPLE 152

2-nonyloxy-7-undecyloxy-1-azaphenanthrene

EXAMPLE 153

2-nonyloxy-7-dodecyloxy-1-azaphenanthrene

EXAMPLE 154

2-decyloxy-7-undecyloxy-1-azaphenanthrene

EXAMPLE 155

2-decyloxy-7-dodecyloxy-1-azaphenanthrene

EXAMPLE 156

2-hexyloxy-7-pentoxy-1-azaphenanthrene

EXAMPLE 157

2-heptyloxy-7-hexyloxy-1-azaphenanthrene

EXAMPLE 158

2-heptyloxy-7-pentoxy-1-azaphenanthrene

EXAMPLE 159

2-octyloxy-7-butoxy-1-azaphenanthrene

EXAMPLE 160

2-octyloxy-7-pentoxy-1-azaphenanthrene

EXAMPLE 161

2-octyloxy-7-hexyloxy-1-azaphenanthrene

EXAMPLE 162

2-octyloxy-7-heptyloxy-1-azaphenanthrene

EXAMPLE 163

2-nonyloxy-7-pentoxy-1-azaphenanthrene

EXAMPLE 164

2-nonyloxy-7-hexyloxy-1-azaphenanthrene

EXAMPLE 165

2-nonyloxy-7-heptyloxy-1-azaphenanthrene

EXAMPLE 166

2-nonyloxy-7-octyloxy-1-azaphenanthrene

EXAMPLE 167

2-butoxy-7-pentoxy-8-fluoro-1-azaphenanthrene

EXAMPLE 168

2-butoxy-7-hexyloxy-8-fluoro-1-azaphenanthrene

EXAMPLE 169

2-butoxy-7-heptyloxy-8-fluoro-1-azaphenanthrene

EXAMPLE 170

2-butoxy-7-octyloxy-8-fluoro-1-azaphenanthrene

EXAMPLE 171

2-butoxy-7-nonyloxy-8-fluoro-1-azaphenanthrene

EXAMPLE 172

2-butoxy-7-decyloxy-8-fluoro-1-azaphenanthrene

EXAMPLE 173

2-pentoxy-7-hexyloxy-8-fluoro-1-azaphenanthrene

EXAMPLE 174

2-pentoxy-7-heptyloxy-8-fluoro-1-azaphenanthrene

EXAMPLE 175

2-pentoxy-7-octyloxy-8-fluoro-1-azaphenanthrene

EXAMPLE 176

2-pentoxy-7-nonyloxy-8-fluoro-1-azaphenanthrene

EXAMPLE 177

2-pentoxy-7-decyloxy-8-fluoro-1-azaphenanthrene

EXAMPLE 178

2-hexyloxy-7-heptyloxy-8-fluoro-1-azaphenanthrene

EXAMPLE 178A 2,7-bis(hexyloxy)-8-fluoro-1-azaphenanthrene; phase sequence X 86 (80 $S_A$ 84) I

EXAMPLE 179

2-hexyloxy-7-octyloxy-8-fluoro-1-azaphenanthrene

EXAMPLE 180

2-hexyloxy-7-nonyloxy-8-fluoro-1-azaphenanthrene

EXAMPLE 181

2-hexyloxy-7-decyloxy-8-fluoro-1-azaphenanthrene

EXAMPLE 182

2-hexyloxy-7-(4-butyldimethylsilyl)butoxy-8-fluoro-1-azaphenanthrene

EXAMPLE 183

2-heptyloxy-7-octyloxy-8-fluoro-1-azaphenanthrene

EXAMPLE 184

2-heptyloxy-7-nonyloxy-8-fluoro-1-azaphenanthrene

EXAMPLE 185

2-heptyloxy-7-decyloxy-8-fluoro-1-azaphenanthrene

EXAMPLE 186

2-heptyloxy-7-(6-methyl)octyloxy-8-fluoro-1-azaphenanthrene

EXAMPLE 187

2-octyloxy-7-nonyloxy-8-fluoro-1-azaphenanthrene

EXAMPLE 188

2-octyloxy-7-decyloxy-8-fluoro-1-azaphenanthrene

EXAMPLE 189

2-octyloxy-7-undecyloxy-8-fluoro-1-azaphenanthrene

EXAMPLE 190

2-octyloxy-7-dodecyloxy-8-fluoro-1-azaphenanthrene

EXAMPLE 191

2-octyloxy-7-(5-oxa)nonyloxy-8-fluoro-1-azaphenanthrene

EXAMPLE 192

2-nonyloxy-7-decyloxy-8-fluoro-1-azaphenanthrene

EXAMPLE 193

2-nonyloxy-7-undecyloxy-8-fluoro-1-azaphenanthrene

EXAMPLE 194

2-nonyloxy-7-dodecyloxy-8-fluoro-1-azaphenanthrene

EXAMPLE 195

2-decyloxy-7-undecyloxy-8-fluoro-1-azaphenanthrene

EXAMPLE 196

2-decyloxy-7-dodecyloxy-8-fluoro-1-azaphenanthrene

EXAMPLE 197

2-hexyloxy-7-pentoxy-8-fluoro-1-azaphenanthrene

EXAMPLE 198

2-heptyloxy-7-hexyloxy-8-fluoro-1-azaphenanthrene

EXAMPLE 199

2-heptyloxy-7-pentoxy-8-fluoro-1-azaphenanthrene

EXAMPLE 200

2-octyloxy-7-butoxy-8-fluoro-1-azaphenanthrene

EXAMPLE 201

2-octyloxy-7-pentoxy-8-fluoro-1-azaphenanthrene

EXAMPLE 202

2-octyloxy-7-hexyloxy-8-fluoro-1-azaphenanthrene

EXAMPLE 203

2-octyloxy-7-heptyloxy-8-fluoro-1-azaphenanthrene

EXAMPLE 204

2-nonyloxy-7-pentoxy-8-fluoro-1-azaphenanthrene

EXAMPLE 205

2-nonyloxy-7-hexyloxy-8-fluoro-1-azaphenanthrene

EXAMPLE 206

2-nonyloxy-7-heptyloxy-8-fluoro-1-azaphenanthrene

EXAMPLE 207

2-nonyloxy-7-octyloxy-8-fluoro-1-azaphenanthrene

EXAMPLE 207A 2-hexyloxy-8-fluoro-1-azaphenanthrene; m.p. 68° C.

EXAMPLE 208

1,8-difluoro-2,7-dioctyloxy-9,10-dihydrophenanthrene

A solution of 0.7 g of 1,8-difluoro-2,7-dioctyloxyphenanthrene in 50 ml of THF hydrogenated at atmospheric pressure at 20° C. with addition of 0.1 g of Pd/C (5% by weight). The catalyst is filtered off, the solvent is removed by vacuum distillation, and the residue is chromatographed on silica gel using dichloromethane. Recrystallization from acetonitrile gives 0.4 g of 1,8-difluoro-2,7-dioctyloxy-9,10-dihydrophenanthrene.

The following are obtained analogously:

EXAMPLE 209

1,8-difluoro-2,7-dibutoxy-9,10-dihydrophenanthrene

EXAMPLE 210

1,8-difluoro-2,7-dipentoxy-9,10-dihydrophenanthrene

EXAMPLE 211

1,8-difluoro-2,7-dihexyloxy-9,10-dihydrophenanthrene; m.p. 63° C.

EXAMPLE 212

1,8-difluoro-2,7-diheptyloxy-9,10-dihydrophenanthrene

EXAMPLE 213

1,8-difluoro-2,7-dinonyloxy-9,10-dihydrophenanthrene

EXAMPLE 214

1,8-difluoro-2,7-didecyloxy-9,10-dihydrophenanthrene

EXAMPLE 215

1,8-difluoro-2,7-diundecyloxy-9,10-dihydrophenanthrene

EXAMPLE 216

1,8-difluoro-2,7-didodecyloxy-9,10-dihydrophenanthrene

EXAMPLE 217

1,8-difluoro-2-butoxy-7-pentoxy-9,10-dihydrophenanthrene

EXAMPLE 218

1,8-difluoro-2-butoxy-7-hexyloxy-9,10-dihydrophenanthrene

EXAMPLE 219

1,8-difluoro-2-butoxy-7-heptoxy-9,10-dihydrophenanthrene

EXAMPLE 220

1,8-difluoro-2-butoxy-7-octyloxy-9,10-dihydrophenanthrene

EXAMPLE 221

1,8-difluoro-2-butoxy-7-nonyloxy-9,10-dihydrophenanthrene

EXAMPLE 222

1,8-difluoro-2-pentoxy-7-propoxy-9,10-dihydrophenanthrene

EXAMPLE 223

1,8-difluoro-2-pentoxy-7-hexyloxy-9,10-dihydrophenanthrene

EXAMPLE 224

1,8-difluoro-2-pentoxy-7-heptyloxy-9,10-dihydrophenanthrene

EXAMPLE 225

1,8-difluoro-2-pentoxy-7-octyloxy-9,10-dihydrophenanthrene

EXAMPLE 226

1,8-difluoro-2-pentoxy-7-nonyloxy-9,10-dihydrophenanthrene

EXAMPLE 227

1,8-difluoro-2-hexyloxy-7-propoxy-9,10-dihydrophenanthrene

EXAMPLE 228

1,8-difluoro-2-hexyloxy-7-heptyloxy-9,10-dihydrophenanthrene

EXAMPLE 229

1,8-difluoro-2-hexyloxy-7-octyloxy-9,10-dihydrophenanthrene

EXAMPLE 230

1,8-difluoro-2-hexyloxy-7-nonyloxy-9,10-dihydrophenanthrene

EXAMPLE 231

1,8-difluoro-2-hexyloxy-7-decyloxy-9,10-dihydrophenanthrene

EXAMPLE 232

1,8-difluoro-2-hexyloxy-7-dodecyloxy-9,10-dihydrophenanthrene

EXAMPLE 233

1,8-difluoro-2-heptyloxy-7-propoxy-9,10-dihydrophenanthrene

EXAMPLE 234

1,8-difluoro-2-heptyloxy-7-octyloxy-9,10-dihydrophenanthrene

EXAMPLE 235

1,8-difluoro-2-heptyloxy-7-nonyloxy-9,10-dihydrophenanthrene

EXAMPLE 236

1,8-difluoro-2-octyloxy-7-ethoxy-9,10-dihydrophenanthrene

EXAMPLE 237

1,8-difluoro-2-octyloxy-7-propoxy-9,10-dihydrophenanthrene

EXAMPLE 238

1,8-difluoro-2-octyloxy-7-nonyloxy-9,10-dihydrophenanthrene

EXAMPLE 239

1,8-difluoro-2-octyloxy-7-decyloxy-9,10-dihydrophenanthrene

EXAMPLE 240

1,8-difluoro-2-nonyloxy-7-ethoxy-9,10-dihydrophenanthrene

EXAMPLE 241
1,8-difluoro-2-nonyloxy-7-propoxy-9,10-dihydrophenanthrene

EXAMPLE 242
1,8-difluoro-2-nonyloxy-7-decyloxy-9,10-dihydrophenanthrene

EXAMPLE 243
1,8-difluoro-2-decyloxy-7-methoxy-9,10-dihydrophenanthrene

EXAMPLE 244
1,8-difluoro-2-decyloxy-7-ethoxy-9,10-dihydrophenanthrene

EXAMPLE 245
1,8-difluoro-2-decyloxy-7-propoxy-9,10-dihydrophenanthrene

EXAMPLE 246
1,8-difluoro-2-decyloxy-7-butoxy-9,10-dihydrophenanthrene

EXAMPLE 247
1,8-difluoro-2-decyloxy-7-pentoxy-9,10-dihydrophenanthrene

EXAMPLE 248
1,8-difluoro-2-decyloxy-7-heptyloxy-9,10-dihydrophenanthrene

EXAMPLE 249
1-fluoro-2,7-dibutoxy-9,10-dihydrophenanthrene

EXAMPLE 250
1-fluoro-2,7-dipentoxy-9,10-dihydrophenanthrene

EXAMPLE 251
1-fluoro-2,7-dihexyloxy-9,10-dihydrophenanthrene

EXAMPLE 252
1-fluoro-2,7-diheptyloxy-9,10-dihydrophenanthrene

EXAMPLE 253
1-fluoro-2,7-dioctyloxy-9,10-dihydrophenanthrene

EXAMPLE 254
1-fluoro-2,7-dinonyloxy-9,10-dihydrophenanthrene

EXAMPLE 255
1-fluoro-2,7-didecyloxy-9,10-dihydrophenanthrene

EXAMPLE 256
1-fluoro-2,7-diundecyloxy-9,10-dihydrophenanthrene

EXAMPLE 257
1-fluoro-2,7-didodecyloxy-9,10-dihydrophenanthrene

EXAMPLE 258
1-fluoro-2-butoxy-7-pentoxy-9,10-dihydrophenanthrene

EXAMPLE 259
1-fluoro-2-butoxy-7-hexyloxy-9,10-dihydrophenanthrene

EXAMPLE 260
1-fluoro-2-butoxy-7-heptyloxy-9,10-dihydrophenanthrene

EXAMPLE 261
1-fluoro-2-butoxy-7-octyloxy-9,10-dihydrophenanthrene

EXAMPLE 262
1-fluoro-2-butoxy-7-nonyloxy-9,10-dihydrophenanthrene

EXAMPLE 263
1-fluoro-2-butoxy-7-decyloxy-9,10-dihydrophenanthrene

EXAMPLE 264
1-fluoro-2-pentoxy-7-hexyloxy-9,10-dihydrophenanthrene

EXAMPLE 265
1-fluoro-2-pentoxy-7-heptyloxy-9,10-dihydrophenanthrene

EXAMPLE 266
1-fluoro-2-pentoxy-7-octyloxy-9,10-dihydrophenanthrene

EXAMPLE 267
1-fluoro-2-pentoxy-7-nonyloxy-9,10-dihydrophenanthrene

EXAMPLE 268
1-fluoro-2-hexyloxy-7-butoxy-9,10-dihydrophenanthrene

EXAMPLE 269
1-fluoro-2-hexyloxy-7-pentoxy-9,10-dihydrophenanthrene

EXAMPLE 270
1-fluoro-2-hexyloxy-7-heptyloxy-9,10-dihydrophenanthrene

EXAMPLE 271
1-fluoro-2-hexyloxy-7-octyloxy-9,10-dihydrophenanthrene

EXAMPLE 272
1-fluoro-2-hexyloxy-7-nonyloxy-9,10-dihydrophenanthrene

EXAMPLE 273
1-fluoro-2-hexyloxy-7-decyloxy-9,10-dihydrophenanthrene

EXAMPLE 274
1-fluoro-2-heptyloxy-7-propoxy-9,10-dihydrophenanthrene

EXAMPLE 275
1-fluoro-2-heptyloxy-7-butoxy-9,10-dihydrophenanthrene

EXAMPLE 276
1-fluoro-2-heptyloxy-7-pentoxy-9,10-dihydrophenanthrene

EXAMPLE 277
1-fluoro-2-heptyloxy-7-octyloxy-9,10-dihydrophenanthrene

EXAMPLE 278
1-fluoro-2-heptyloxy-7-nonyloxy-9,10-dihydrophenanthrene

EXAMPLE 279
1-fluoro-2-heptyloxy-7-decyloxy-9,10-dihydrophenanthrene

EXAMPLE 280
1-fluoro-2-octyloxy-7-propoxy-9,10-dihydrophenanthrene

EXAMPLE 281
1-fluoro-2-octyloxy-7-butoxy-9,10-dihydrophenanthrene

EXAMPLE 282
1-fluoro-2-octyloxy-7-pentoxy-9,10-dihydrophenanthrene

EXAMPLE 283
1-fluoro-2-octyloxy-7-hexyloxy-9,10-dihydrophenanthrene

EXAMPLE 284
1-fluoro-2-octyloxy-7-octyloxy-9,10-dihydrophenanthrene

EXAMPLE 285
1-fluoro-2-octyloxy-7-nonyloxy-9,10-dihydrophenanthrene

EXAMPLE 286
1-fluoro-2-octyloxy-7-decyloxy-9,10-dihydrophenanthrene

EXAMPLE 287
1-fluoro-2-octyloxy-7-undecyloxy-9,10-dihydrophenanthrene

EXAMPLE 288
1-fluoro-2-nonyloxy-7-propoxy-9,10-dihydrophenanthrene

EXAMPLE 289
1-fluoro-2-nonyloxy-7-butoxy-9,10-dihydrophenanthrene

EXAMPLE 290
1-fluoro-2-nonyloxy-7-pentoxy-9,10-dihydrophenanthrene

EXAMPLE 291
1-fluoro-2-nonyloxy-7-hexyloxy-9,10-dihydrophenanthrene

EXAMPLE 292
1-fluoro-2-nonyloxy-7-heptyloxy-9,10-dihydrophenanthrene

EXAMPLE 293
1-fluoro-2-nonyloxy-7-octyloxy-9,10-dihydrophenanthrene

EXAMPLE 294
1-fluoro-2-nonyloxy-7-decyloxy-9,10-dihydrophenanthrene

EXAMPLE 295
2,7-bis(pentoxy)-1,8-diaza-9,10-dihydrophenanthrene

EXAMPLE 296
2,7-bis(heptyloxy)-1,8-diaza-9,10-dihydrophenanthrene

EXAMPLE 297
2,7-bis(octyloxy)-1,8-diaza-9,10-dihydrophenanthrene

EXAMPLE 298
2,7-bis(nonyloxy)-1,8-diaza-9,10-dihydrophenanthrene

EXAMPLE 299
2,7-bis(decyloxy)-1,8-diaza-9,10-dihydrophenanthrene

EXAMPLE 300
2,7-bis(undecyloxy)-1,8-diaza-9,10-dihydrophenanthrene

EXAMPLE 301
2,7-bis(dodecyloxy)-1,8-diaza-9,10-dihydrophenanthrene

EXAMPLE 302
2-butoxy-7-pentoxy-1,8-diaza-9,10-dihydrophenanthrene

EXAMPLE 303
2-butoxy-7-hexyloxy-1,8-diaza-9,10-dihydrophenanthrene

EXAMPLE 304
2-butoxy-7-heptyloxy-1,8-diaza-9,10-dihydrophenanthrene

EXAMPLE 305
2-butoxy-7-octyloxy-1,8-diaza-9,10-dihydrophenanthrene

EXAMPLE 306
2-butoxy-7-nonyloxy-1,8-diaza-9,10-dihydrophenanthrene

EXAMPLE 307
2-butoxy-7-decyloxy-1,8-diaza-9,10-dihydrophenanthrene

EXAMPLE 308
2-pentoxy-7-hexyloxy-1,8-diaza-9,10-dihydrophenanthrene

EXAMPLE 309
2-pentoxy-7-heptyloxy-1,8-diaza-9,10-dihydrophenanthrene

EXAMPLE 310
2-pentoxy-7-octyloxy-1,8-diaza-9,10-dihydrophenanthrene

EXAMPLE 311
2-pentoxy-7-nonyloxy-1,8-diaza-9,10-dihydrophenanthrene

EXAMPLE 312
2-pentoxy-7-decyloxy-1,8-diaza-9,10-dihydrophenanthrene

EXAMPLE 313

2-hexyloxy-7-heptyloxy-1,8-diaza-9,10-dihydrophenanthrene

EXAMPLE 314

2-hexyloxy-7-octyloxy-1,8-diaza-9,10-dihydrophenanthrene

EXAMPLE 315

2-hexyloxy-7-nonyloxy-1,8-diaza-9,10-dihydrophenanthrene

EXAMPLE 316

2-hexyloxy-7-decyloxy-1,8-diaza-9,10-dihydrophenanthrene

EXAMPLE 317

2-hexyloxy-7-(4-butyldimethylsilyl)butoxy-1,8-diaza-9,10-dihydrophenanthrene

EXAMPLE 318

2-heptyloxy-7-octyloxy-1,8-diaza-9,10-dihydrophenanthrene

EXAMPLE 319

2-heptyloxy-7-nonyloxy-1,8-diaza-9,10-dihydrophenanthrene

EXAMPLE 320

2-heptyloxy-7-decyloxy-1,8-diaza-9,10-dihydrophenanthrene

EXAMPLE 321

2-heptyloxy-7-(6-methyl)octyloxy-1,8-diaza-9,10-dihydrophenanthrene

EXAMPLE 322

2-octyloxy-7-nonyloxy-1,8-diaza-9,10-dihydrophenanthrene

EXAMPLE 323

2-octyloxy-7-decyloxy-1,8-diaza-9,10-dihydrophenanthrene

EXAMPLE 324

2-octyloxy-7-undecyloxy-1,8-diaza-9,10-dihydrophenanthrene

EXAMPLE 325

2-octyloxy-7-dodecyloxy-1,8-diaza-9,10-dihydrophenanthrene

EXAMPLE 326

2-octyloxy-7-(5-oxa)nonyloxy-1,8-diaza-9,10-dihydrophenanthrene

EXAMPLE 327

2-nonyloxy-7-decyloxy-1,8-diaza-9,10-dihydrophenanthrene

EXAMPLE 328

2-nonyloxy-7-undecyloxy-1,8-diaza-9,10-dihydrophenanthrene

EXAMPLE 329

2-nonyloxy-7-dodecyloxy-1,8-diaza-9,10-dihydrophenanthrene

EXAMPLE 330

2-decyloxy-7-undecyloxy-1,8-diaza-9,10-dihydrophenanthrene

EXAMPLE 331

2-decyloxy-7-dodecyloxy-1,8-diaza-9,10-dihydrophenanthrene

EXAMPLE 332

2-butoxy-7-pentoxy-1-aza-9,10-dihydrophenanthrene

EXAMPLE 333

2-butoxy-7-hexyloxy-1-aza-9,10-dihydrophenanthrene

EXAMPLE 334

2-butoxy-7-heptyloxy-1-aza-9,10-dihydrophenanthrene

EXAMPLE 335

2-butoxy-7-octyloxy-1-aza-9,10-dihydrophenanthrene

EXAMPLE 336

2-butoxy-7-nonyloxy-1-aza-9,10-dihydrophenanthrene

EXAMPLE 337

2-butoxy-7-decyloxy-1-aza-9,10-dihydrophenanthrene

EXAMPLE 338

2-pentoxy-7-hexyloxy-1-aza-9,10-dihydrophenanthrene

EXAMPLE 339

2-pentoxy-7-heptyloxy-1-aza-9,10-dihydrophenanthrene

EXAMPLE 340

2-pentoxy-7-octyloxy-1-aza-9,10-dihydrophenanthrene

EXAMPLE 341

2-pentoxy-7-nonyloxy-1-aza-9,10-dihydrophenanthrene

EXAMPLE 342

2-pentoxy-7-decyloxy-1-aza-9,10-dihydrophenanthrene

EXAMPLE 343

2-hexyloxy-7-heptyloxy-1-aza-9,10-dihydrophenanthrene

EXAMPLE 344
2-hexyloxy-7-octyloxy-1-aza-9,10-dihydrophenanthrene

EXAMPLE 345
2-hexyloxy-7-nonyloxy-1-aza-9,10-dihydrophenanthrene

EXAMPLE 346
2-hexyloxy-7-decyloxy-1-aza-9,10-dihydrophenanthrene

EXAMPLE 347
2-hexyloxy-7-(4-butyldimethylsilyl)butoxy-1-aza-9,10-dihydrophenanthrene

EXAMPLE 348
2-heptyloxy-7-octyloxy-1-aza-9,10-dihydrophenanthrene

EXAMPLE 349
2-heptyloxy-7-nonyloxy-1-aza-9,10-dihydrophenanthrene

EXAMPLE 350
2-heptyloxy-7-decyloxy-1-aza-9,10-dihydrophenanthrene

EXAMPLE 351
2-heptyloxy-7-(6-methyl)octyloxy-1-aza-9,10-dihydrophenanthrene

EXAMPLE 352
2-octyloxy-7-nonyloxy-1-aza-9,10-dihydrophenanthrene

EXAMPLE 353
2-octyloxy-7-decyloxy-1-aza-9,10-dihydrophenanthrene

EXAMPLE 354
2-octyloxy-7-undecyloxy-1-aza-9,10-dihydrophenanthrene

EXAMPLE 355
2-octyloxy-7-dodecyloxy-1-aza-9,10-dihydrophenanthrene

EXAMPLE 356
2-octyloxy-7-(5-oxa)nonyloxy-1-aza-9,10-dihydrophenanthrene

EXAMPLE 357
2-nonyloxy-7-decyloxy-1-aza-9,10-dihydrophenanthrene

EXAMPLE 358
2-nonyloxy-7-undecyloxy-1-aza-9,10-dihydrophenanthrene

EXAMPLE 359
2-nonyloxy-7-dodecyloxy-1-aza-9,10-dihydrophenanthrene

EXAMPLE 360
2-decyloxy-7-undecyloxy-1-aza-9,10-dihydrophenanthrene

EXAMPLE 361
2-decyloxy-7-dodecyloxy-1-aza-9,10-dihydrophenanthrene

EXAMPLE 362
2-hexyloxy-7-pentoxy-1-aza-9,10-dihydrophenanthrene

EXAMPLE 363
2-heptyloxy-7-hexyloxy-1-aza-9,10-dihydrophenanthrene

EXAMPLE 364
2-heptyloxy-7-pentoxy-1-aza-9,10-dihydrophenanthrene

EXAMPLE 365
2-octyloxy-7-butoxy-1-aza-9,10-dihydrophenanthrene

EXAMPLE 366
2-octyloxy-7-pentoxy-1-aza-9,10-dihydrophenanthrene

EXAMPLE 367
2-octyloxy-7-hexyloxy-1-aza-9,10-dihydrophenanthrene

EXAMPLE 368
2-octyloxy-7-heptyloxy-1-aza-9,10-dihydrophenanthrene

EXAMPLE 369
2-nonyloxy-7-pentoxy-1-aza-9,10-dihydrophenanthrene

EXAMPLE 370
2-nonyloxy-7-hexyloxy-1-aza-9,10-dihydrophenanthrene

EXAMPLE 371
2-nonyloxy-7-heptyloxy-1-aza-9,10-dihydrophenanthrene

EXAMPLE 372
2-nonyloxy-7-octyloxy-1-aza-9,10-dihydrophenanthrene

EXAMPLE 373
2-butoxy-7-pentoxy-8-fluoro-1-aza-9,10-dihydrophenanthrene

EXAMPLE 374
2-butoxy-7-hexyloxy-8-fluoro-1-aza-9,10-dihydrophenanthrene

EXAMPLE 375
2-butoxy-7-heptyloxy-8-fluoro-1-aza-9,10-dihydrophenanthrene

EXAMPLE 376
2-butoxy-7-octyloxy-8-fluoro-1-aza-9,10-dihydrophenanthrene

EXAMPLE 377
2-butoxy-7-nonyloxy-8-fluoro-1-aza-9,10-dihydrophenanthrene

EXAMPLE 378
2-butoxy-7-decyloxy-8-fluoro-1-aza-9,10-dihydrophenanthrene

EXAMPLE 379
2-pentoxy-7-hexyloxy-8-fluoro-1-aza-9,10-dihydrophenanthrene

EXAMPLE 380
2-pentoxy-7-heptyloxy-8-fluoro-1-aza-9,10-dihydrophenanthrene

EXAMPLE 381
2-pentoxy-7-octyloxy-8-fluoro-1-aza-9,10-dihydrophenanthrene

EXAMPLE 382
2-pentoxy-7-nonyloxy-8-fluoro-1-aza-9,10-dihydrophenanthrene

EXAMPLE 383
2-pentoxy-7-decyloxy-8-fluoro-1-aza-9,10-dihydrophenanthrene

EXAMPLE 384
2-hexyloxy-7-heptyloxy-8-fluoro-1-aza-9,10-dihydrophenanthrene

EXAMPLE 385
2-hexyloxy-7-octyloxy-8-fluoro-1-aza-9,10-dihydrophenanthrene

EXAMPLE 386
2-hexyloxy-7-nonyloxy-8-fluoro-1-aza-9,10-dihydrophenanthrene

EXAMPLE 387
2-hexyloxy-7-decyloxy-8-fluoro-1-aza-9,10-dihydrophenanthrene

EXAMPLE 388
2-hexyloxy-7-(4-butyldimethylsilyl)butoxy-8-fluoro-1-aza-9,10-dihydrophenanthrene

EXAMPLE 389
2-heptyloxy-7-octyloxy-8-fluoro-1-aza-9,10-dihydrophenanthrene

EXAMPLE 390
2-heptyloxy-7-nonyloxy-8-fluoro-1-aza-9,10-dihydrophenanthrene

EXAMPLE 391
2-heptyloxy-7-decyloxy-8-fluoro-1-aza-9,10-dihydrophenanthrene

EXAMPLE 392
2-heptyloxy-7-(6-methyl)octyloxy-8-fluoro-1-aza-9,10-dihydrophenanthrene

EXAMPLE 393
2-octyloxy-7-nonyloxy-8-fluoro-1-aza-9,10-dihydrophenanthrene

EXAMPLE 394
2-octyloxy-7-decyloxy-8-fluoro-1-aza-9,10-dihydrophenanthrene

EXAMPLE 395
2-octyloxy-7-undecyloxy-8-fluoro-1-aza-9,10-dihydrophenanthrene

EXAMPLE 396
2-octyloxy-7-dodecyloxy-8-fluoro-1-aza-9,10-dihydrophenanthrene

EXAMPLE 397
2-octyloxy-7-(5-oxa)nonyloxy-8-fluoro-1-aza-9,10-dihydrophenanthrene

EXAMPLE 398
2-nonyloxy-7-decyloxy-8-fluoro-1-aza-9,10-dihydrophenanthrene

EXAMPLE 399
2-nonyloxy-7-undecyloxy-8-fluoro-1-aza-9,10-dihydrophenanthrene

EXAMPLE 400
2-nonyloxy-7-dodecyloxy-8-fluoro-1-aza-9,10-dihydrophenanthrene

EXAMPLE 401
2-decyloxy-7-undecyloxy-8-fluoro-1-aza-9,10-dihydrophenanthrene

EXAMPLE 402
2-decyloxy-7-dodecyloxy-8-fluoro-1-aza-9,10-dihydrophenanthrene

EXAMPLE 403
2-hexyloxy-7-pentoxy-8-fluoro-1-aza-9,10-dihydrophenanthrene

EXAMPLE 404
2-heptyloxy-7-hexyloxy-8-fluoro-1-aza-9,10-dihydrophenanthrene

EXAMPLE 405
2-heptyloxy-7-pentoxy-8-fluoro-1-aza-9,10-dihydrophenanthrene

EXAMPLE 406
2-octyloxy-7-butoxy-8-fluoro-1-aza-9,10-dihydrophenanthrene

EXAMPLE 407

2-octyloxy-7-pentoxy-8-fluoro-1-aza-9,10-dihydrophenanthrene

EXAMPLE 408

2-octyloxy-7-hexyloxy-8-fluoro-1-aza-9,10-dihydrophenanthrene

EXAMPLE 409

2-octyloxy-7-heptyloxy-8-fluoro-1-aza-9,10-dihydrophenanthrene

EXAMPLE 410

2-nonyloxy-7-pentoxy-8-fluoro-1-aza-9,10-dihydrophenanthrene

EXAMPLE 411

2-nonyloxy-7-hexyloxy-8-fluoro-1-aza-9,10-dihydrophenanthrene

EXAMPLE 412

2-nonyloxy-7-heptyloxy-8-fluoro-1-aza-9,10-dihydrophenanthrene

EXAMPLE 413

2-nonyloxy-7-octyloxy-8-fluoro-1-aza-9,10-dihydrophenanthrene

Use Example 1

A liquid-crystal mixture (TLC 1; Hoechst AG) having the phase transition temperatures $S_C/S_A$ 79° C., $S_A/N$ 91° C. and N/I 101° C. is mixed with 10% by weight of the compound from Example 76, giving the phase transition temperatures $S_C/S_A$ 76° C., $S_A/N$ 93° C. and N/I 102° C.

Use Example 2

10% by weight of the compound from Example 178A are dissolved in TLC 1, giving the phase transition temperatures $S_C/S_A$ 69° C., $S_A/N$ 88° C. and N/I 100° C.

Use Example 3

10% by weight of the compound from Example 4 are dissolved in TLC 1, giving the phase transition temperatures $S_C/S_A$ 71° C., $S_A/N$ 92° C. and N/I 102° C.

We claim:

1. A phenanthrene derivative of the formula (I),

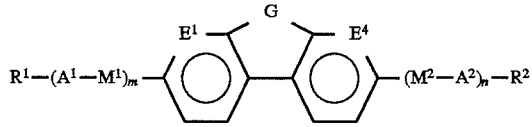

in which the symbols and indices have the following meanings:

$E^1$ and $E^4$, independently of one another, are —N—, CF or —CH— with the proviso that at least one of $E^1$ and $E^4$ must be —N— or —CF—;

G is the —CH$_2$—CH$_2$— or —CH=CH— group;

$R^1$ and $R^2$, independently of one another, are hydrogen, —F, or a straight-chain or branched alkyl radical having 1 to 20 carbon atoms (with or without asymmetrical carbon atoms), where one or more —CH$_2$— groups may also be replaced by —O—, —CO—, —CH=CH—, —C≡C—,

—Si(CH$_3$)$_2$—, 1,4-phenylene, trans-1,4-cyclohexylene, with the proviso that oxygen atoms must not be bonded directly to one another, or one or more H atoms of the alkyl radical may be substituted by —F, with the proviso that $R^1$ and $R^2$ must not both be hydrogen;

$M^1$ and $M^2$ are identical or different and are —CO—O—, —O—CO—, —CH$_2$—O—, —O—CH$_2$—, —CH$_2$—CH$_2$—, —C≡C— or a single bond;

$A^1$ and $A^2$ are identical or different and are 1,4-phenylene, in which one or more H atoms may be replaced by F; pyridine-2,5-diyl, in which one or more H atoms may be replaced by F; pyrimidine-2,5-diyl, in which one H atom may be replaced by F; trans-1,4-cyclohexylene, in which one H atom may be replaced by CN; 1,3,4-thiadiazole-2,5-diyl; 1,3-dioxane-2,5-diyl;

n and m are zero or one, but add up to 1 at most.

2. A phenanthrene derivative of the formula (I) as claimed in claim 1, selected from the group consisting of

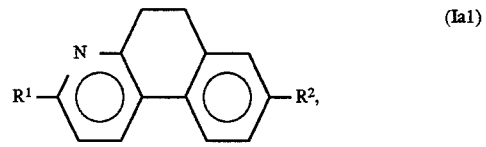
(Ia1)

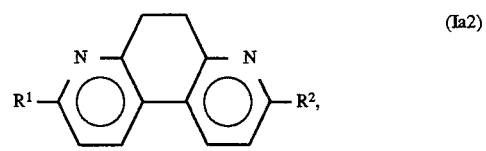
(Ia2)

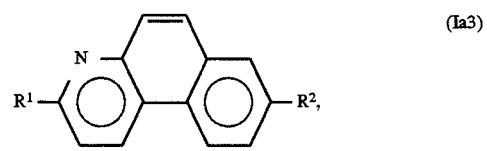
(Ia3)

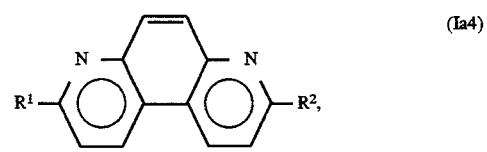
(Ia4)

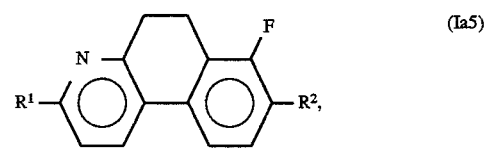
(Ia5)

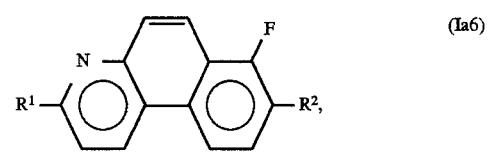
(Ia6)

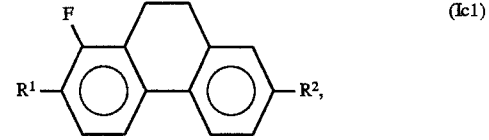
(Ic1)

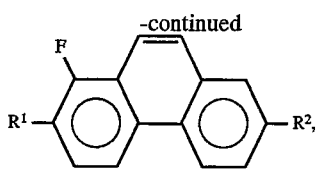 (Ic2)

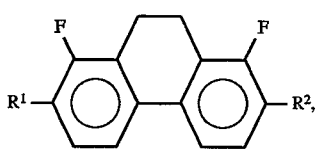 (Ic3)

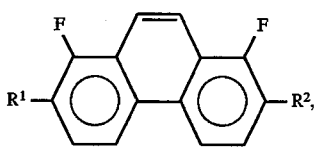 (Ic4)

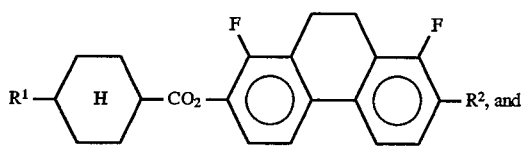 (Ic5)

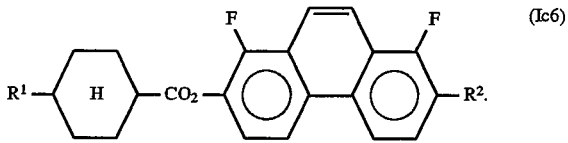 (Ic6)

3. A liquid-crystal mixture comprising one or more compounds of the formula (I) as claimed in claim 1.

4. A liquid-crystal mixture as claimed in claim 3 comprising from 2 to 20 components, including from 1 to 10 compounds of the formula (I).

5. A liquid-crystal mixture as claimed in claim 3 comprising from 0.01 to 80% by weight of one or more compounds of the formula (I).

6. A liquid-crystal mixture as claimed in claim 3, which is ferroelectric.

7. An electro-optical switching or display element comprising a liquid-crystal mixture as claimed in claim 3.

* * * * *